United States Patent
Greter et al.

(10) Patent No.: US 9,045,259 B2
(45) Date of Patent: Jun. 2, 2015

(54) DISCHARGE DEVICE WITH TUBE

(75) Inventors: Andy Greter, Baar (CH); Roger Dubach, Rotkreuz (CH)

(73) Assignee: MEDMIX SYSTEMS AG, Rotkreuz (CH)

( * ) Notice: Subject to any disclaimer, the term of this patent is extended or adjusted under 35 U.S.C. 154(b) by 954 days.

(21) Appl. No.: 13/201,363

(22) PCT Filed: Feb. 12, 2010

(86) PCT No.: PCT/CH2010/000039
§ 371 (c)(1),
(2), (4) Date: Aug. 12, 2011

(87) PCT Pub. No.: WO2010/091527
PCT Pub. Date: Aug. 19, 2010

(65) Prior Publication Data
US 2011/0295212 A1  Dec. 1, 2011

(30) Foreign Application Priority Data

Feb. 13, 2009 (CH) .......................... 227/09

(51) Int. Cl.
| | |
|---|---|
| A61M 37/00 | (2006.01) |
| B65D 35/30 | (2006.01) |
| A61B 17/00 | (2006.01) |
| A61B 17/88 | (2006.01) |
| B65D 51/22 | (2006.01) |
| B65D 81/32 | (2006.01) |

(Continued)

(52) U.S. Cl.
CPC .......... *B65D 35/30* (2013.01); *A61B 17/00491* (2013.01); *A61B 17/8833* (2013.01); *A61B 2017/00495* (2013.01); *A61B 2017/8838* (2013.01); *A61F 2002/30561* (2013.01); *A61F 2002/30601* (2013.01); *B65D 51/224* (2013.01); *B65D 81/325* (2013.01); *B65D 83/0005* (2013.01)

(58) Field of Classification Search
USPC ........................................ 604/82, 87, 88, 191
See application file for complete search history.

(56) References Cited

U.S. PATENT DOCUMENTS 4,755,169 A * 7/1988 Sarnoff et al. ................ 604/511
5,153,231 A 10/1992 Bouquet et al.
(Continued)

FOREIGN PATENT DOCUMENTS

DE   197 10 878 C1   2/1998
EP   0 352 370 A1    1/1990
(Continued)

OTHER PUBLICATIONS

International Preliminary Report on Patentability issued in corresponding International Patent Application No. PCT/CH2010/000039 dated Aug. 16, 2011.

*Primary Examiner* — Emily Schmidt
(74) *Attorney, Agent, or Firm* — Sughrue Mion, PLLC (57) ABSTRACT

A discharge device for discharging a product from a tube having a delivery outlet and a deformable wall. The discharge device according to the invention comprises a housing with a chamber that has a chamber opening and in which the tube is accommodated. A movable stopper is arranged inside the tube and is placed at the end opposite the delivery outlet and closes this end of the tube. An advancing member can be connected to the stopper and is displaceable inside the tube in the direction of the delivery outlet for discharging the fluid product from the tube.

9 Claims, 6 Drawing Sheets

(51) Int. Cl.
  *B65D 83/00* (2006.01)
  *A61F 2/30* (2006.01)

(56) References Cited

U.S. PATENT DOCUMENTS

| | | | |
|---|---|---|---|
| 5,161,715 | A | 11/1992 | Giannuzzi |
| 6,193,108 | B1 | 2/2001 | Lepsius et al. |
| 2003/0050597 | A1 | 3/2003 | Dodge et al. |
| 2008/0037365 | A1 | 2/2008 | Axelsson et al. |

FOREIGN PATENT DOCUMENTS

| | | |
|---|---|---|
| EP | 0 503 824 A2 | 9/1992 |
| EP | 1 762 507 A2 | 3/2007 |
| WO | 00/10880 A1 | 3/2000 |
| WO | 2004/066784 A2 | 8/2004 |

\* cited by examiner

DISCHARGE DEVICE WITH TUBE

CROSS REFERENCE TO RELATED APPLICATIONS

This application is a National Stage of International Application No. PCT/CH2010/000039 filed Feb. 12, 2010, claiming priority based on Swiss Patent Application No. 00227/09, filed Feb. 13, 2009, the contents of all of which are incorporated herein by reference in their entirety.

TECHNICAL FIELD

The present invention relates to a discharge device for discharging a product from at least one container.

PRIOR ART

In various sectors of medicine, discharge devices are used for discharging a flowable product from a container, wherein the container containing the product can be inserted into a chamber of the discharge device. The container may be, for example, a glass carpule, i.e. a cylindrical glass vessel which is closed at a distal end by a pierceable septum, a displaceable stopper which closes the vessel proximally being inserted into the proximal end of said vessel. A discharge device of this type can be formed with a plurality of chambers for various components of a product and can comprise a mixing device for mixing the components within the discharge device. Devices of this type are used for various tasks, for example for discharging and subsequently mixing different components of a bone cement or for discharging two components of a medicament which is not produced, by mixing of the two components, until immediately prior to administration.

Carpules make it possible to store sensitive products, for example components of medicaments or aggressive substances, such as a bone cement monomer, for a relatively long period of time. However, containers in the form of carpules have various disadvantages. Due to the use of glass, carpules are susceptible to impacts and may break if incorrectly handled. In addition, carpules are relatively expensive to produce. It is therefore desirable to provide a cost-effective and breakproof replacement for carpules, which also makes it possible to store a component of a medicament or another sensitive product for a relatively long time, and to provide a correspondingly adapted discharge device for this purpose. The discharge device is intended to be suitable here especially for use in the medical context.

In order to store flowable products or components, use is often made in other technical sectors of tubes. Tubes are generally formed with a rigid dispensing region and a deformable wall region, wherein the regions may consist of the same material, for example aluminum. Aluminum is suitable as a material since it only interacts to a very small extent, if at all, with the product in the tube. In the deformable wall region, the material of the tube is of such thin design that the wall can be compressed. In the rigid dispensing region, the material of the tube conceals an opening which is opened, for example pierced, in order to dispense the product from the tube. In said region, the tube frequently has a cylindrical joining region which protrudes out of the dispensing region in a longitudinal direction and in which an external thread is formed. A closure cap is frequently screwed onto the external thread.

In order to discharge a product from a tube, use is made in WO 2004/066784 of a discharge device having a squeezing mechanism. The discharge device has a chamber in which the tube is accommodated and is secured against axial displacement along the chamber. The dispensing opening of the tube protrudes out of the chamber. A roller is provided within the chamber, the roller squeezing together the tube, beginning from the end opposite the dispensing opening, against the inner wall of the chamber. The content of the tube is pressed out of the tube by the roller being rolled forward axially in the direction of the dispensing opening by means of a roller drive. A similar discharge device is known from WO 00/10880. However, when tubes are squeezed out in such a manner, metering of the content of the tube is difficult, and a considerable residue may remain in the tube. Furthermore, the tube has to be opened by hand prior to insertion into the discharge device. Mixing of the content of the tube with further components is not shown.

In order to open and empty a tube, an apparatus which serves to mix bone cement is shown in US 2008/0037365 A1. In this apparatus, a mixing chamber is provided with a powder component and has a connection with an internal thread for connecting a tube to a viscous component. A protruding spike which is of cylindrical design and can form a feed line to the interior of the mixing chamber is provided in the connection. The tube has a connecting part which has an external thread and can be connected to the mixing chamber by screwing to the internal thread on said mixing chamber. When the tube is screwed onto the connection of the mixing chamber, the covering of the dispensing opening is pierced by the spike and a fluid connection is produced between the internal volume of the tube and the interior of the mixing chamber. The mixture can subsequently be discharged from the mixing chamber. In order to discharge the product from the tube and to mix said product with further components, a number of actions is required, and the tube has to be squeezed out manually.

EP 1 762 507 discloses a cartridge for discharging a fluid material, for example a sealing compound, which cartridge is provided for use with a gun dispenser. The cartridge has a tubular container with a piston which is displaceable therein. At its front end, the container is provided with a rigid cap and has an outlet opening. The side wall of the container consists of a thin film. In order to discharge the material, the cartridge is secured at the rear end thereof on the dispenser, and the piston is gradually pushed into the cartridge by a ratchet mechanism. However, the dispenser is not suitable for use with conventional tubes and is unsuitable for many applications in the medical context.

It is an object of the present invention to provide a discharge device for discharging a product from a container, in which the product is reliably discharged, the product is made available in a simple manner for further processing and only a few actions are required in order to provide the discharge device with the container. The container is preferably not intended to have to be already opened outside the discharge device.

SUMMARY OF THE INVENTION

According to the present invention, a discharge device for discharging a fluid product from a container with a dispensing opening is provided, wherein the container is designed as a tube with a deformable wall. The device comprises a housing with a chamber in which the tube is accommodated. The chamber has a chamber opening for discharging the product from the discharge device. A movable stopper is arranged in the tube, said stopper being arranged displaceably relative to the tube at the end opposite the dispensing opening and closing said end of the tube. An advancing member can be joined to the stopper and is movable within the tube in the direction of the dispensing opening in order to discharge the fluid product from the tube. The discharge device may be designed, for example, as a syringe with a chamber or preferably also as a multichamber syringe.

The tube is preferably fully accommodated in the chamber. The dimensions of the discharge device are preferably selected in such a manner that the housing can be grasped between two fingers of one hand. The advancing member then has an actuating surface such that the advancing member can be advanced manually by applying pressure to the actuating surface with the thumb of the same hand.

The dispensing opening is preferably provided on a rigid region of the tube, which is adjoined by the deformable region which is provided essentially to accommodate the product. The dispensing opening of the tube can be closed with a pierceable or severable covering. The tube can have an external thread which surrounds the dispensing opening. In this case, the external thread is preferably formed in the rigid region of the tube. The product to be discharged is provided between the closed opening and the stopper. The stopper closes the tube at that end of the tube which is opposite the covered opening, the stopper being displaceable in the longitudinal direction of the tube and ending at the inner circumference of the tube.

The tube is produced, for example, from an aluminum alloy or from fluoropolymers. It can also have a treated surface, for example a coating. These materials have proven particularly suitable for storing chemically aggressive components. For example, they are suitable for accommodating monomers for bone cement without interacting with the monomer. A layer of the material of the tube, as also used for the wall region and the dispensing region, is preferably provided as the covering for the dispensing opening of the tube. In the case of a tube with a dispensing opening which is closed in such a manner, only a single sealing point is produced, specifically between the tube wall and the stopper. However, use may also be made of, for example, plastic or rubber films or membranes for the covering. The coverings may have different thicknesses but should be able to be pierced or severed.

The tube wall preferably bears directly against the inner circumference of the chamber, as a result of which the chamber wall serves as the means of stabilizing the tube wall. Furthermore, the tube wall is held between the inner wall of the chamber and the stopper. In addition, at its rear end opposite the dispensing opening, the tube can have a retaining element which interacts with the chamber in such a manner that displacement of the retaining element in the direction of the dispensing opening is prevented. In this manner, the tube is additionally stabilized in the chamber. The chamber and the tube are preferably of cylindrical design. The tube can be provided interchangeably in the chamber, i.e. as soon as a tube has been emptied, the tube can be removed from the discharge device and a new, filled tube can be inserted. In the process, the advancing member can be interchanged together with the tube or can be joined again to the stopper of a new tube. It is possible to insert a tube which has already been filled into the discharge device, or an empty tube can be placed into the discharge device, and can be subsequently filled and finally the stopper can be inserted into the tube.

By means of the dispensing device according to the invention with a tube, or a system consisting of a dispensing device and a tube, use can be made of the advantages of using tubes to store products or product components, and there is a reliable option of making available the content of the tube for further use. The product can be immediately used, or it can be used for further processing, for example mixing with further components. The discharge device according to the invention provides an exact metering option for this with simple use. By means of the use of a stopper in the tube for discharging the content of the tube from the tube, the operation can be carried out at a higher pressure than with the conventional squeezing processes. There need be no concern that some of the content of the tube will remain in the tube. The tube here is held securely in the discharge device, firstly by means of the chamber wall and secondly by means of the stopper.

A connecting device is preferably provided between the dispensing opening of the tube and the chamber opening, the connecting device connecting the chamber opening to the dispensing opening of the tube. The product can therefore be discharged from the tube directly from the discharge device by means of the connecting device. However, it is also possible to combine further means, for example a second product chamber or a mixing means, with the chamber opening.

The discharge device is preferably designed as a multichamber syringe and has at least two chambers which are arranged parallel to each other, wherein a tube as described above is provided in at least one of the chambers. However, it is also possible for more than two chambers to be arranged in parallel next to one another, and a tube can be provided in each chamber. A piston rod which protrudes out of the chamber at a chamber end which lies opposite the discharge opening can serve as the advancing member. The piston rod can be displaced manually along the longitudinal axis of the chamber. The advancing members for the two or more chambers can be connected to one another preferably at their rear end which faces away from the dispensing opening, or are permanently connected to one another, and have a common actuating surface for a user's thumb.

If the dispensing opening of the tube is still closed when the tube is inserted into the discharge device, an opening device can advantageously be provided in the discharge device, the opening device opening, for example severing or piercing, the covering of the dispensing opening of the tube. The opening device is preferably arranged displaceably relative to the tube. The opening device may be attached to the tube before the latter is inserted into the chamber of the discharge device. As an alternative, it is also possible to provide an opening device within the chamber of the discharge device, said opening device piercing the tube, for example upon insertion into the chamber. Of course, it is in principle also possible to open the tube prior to the insertion into the chamber.

In one embodiment, the tube is mounted movably in the chamber of the discharge device, and an actuating element is provided for advancing the tube relative to the chamber in the direction of the discharge opening. The actuating element may be identical to the advancing member for the stopper and preferably acts directly on the stopper in the tube in order to advance the tube in the chamber of the discharge device. In this case, force for advancing the closed tube relative to the chamber is transmitted via the incompressible product. In principle, however, it is also possible for the actuating element to first of all act on part of the tube, as long as the tube opening is closed, in order to advance the tube, and after the tube opening has been opened, is recoupled in such a manner that the actuating element acts on the stopper of the tube in order to discharge the product from the tube.

The opening device preferably has a puncturing element which is provided for piercing or severing the covering of the tube opening when the tube is advanced relative to the puncturing element. The puncturing element can be provided, for example, as a cannula or as a spike with a passage or a passage line which are arranged on a holder which can be placed onto the tube in the region of the covered opening of the tube. If the puncturing element is advanced relative to the tube, the cannula or the spike pierces the covering of the tube opening, thus producing access to the interior of the tube.

The puncturing element is preferably arranged on the tube in such a manner that, in a first position, it can be displaced together with the tube relative to the chamber and, in a second position, abuts in the advancing direction against a stop of the chamber, and therefore is stationary relative to the chamber and can be displaced relative to the tube. Accordingly, the puncturing element is displaced in the advancing direction together with the tube relative to the chamber of the discharge device when the actuating element acts on the tube or on the stopper. As soon as the puncturing element abuts against the stop of the chamber, it is prevented from advancing further, and therefore the advancing force acts solely on the tube and advances the latter relative to the puncturing element and to the chamber. In this case, the cannula or the spike of the puncturing element is moved towards the covering of the tube opening until it pierces or severs said covering. A further stop for the tube is provided on the puncturing element or else on the chamber, against which stop the tube abuts as soon as the puncturing element has pierced the covering of the tube opening such that the tube is also stationary relative to the chamber and the advancing force of the actuating element in the form of the actuating member acts solely on the stopper in the tube, and therefore the product can be discharged from the tube through the opening or through the cannula. The output of the passage of the puncturing element, through which the product is discharged from the tube or from the puncturing element, preferably comes to lie opposite the discharge opening of the chamber, and therefore the product can be fully discharged from the discharge device. A seal is preferably provided between the discharge opening of the chamber and the puncturing element in such a manner that the transition between the puncturing element and the discharge opening is sealed off to the outside as soon as the puncturing element abuts against the stop in the chamber. The opening device, or the puncturing element, can therefore serve as the connecting device which connects the chamber opening of the discharge device to the dispensing opening of the tube.

As described above, the puncturing element is preferably arranged movably at the end of the tube with the covered opening. The puncturing element here preferably comes to lie in front of the covering, in the first position, and, in the second position in which the puncturing element is displaced relative to the tube, comes to lie in a position in which the covering of the opening is pierced. The puncturing element can therefore advantageously be arranged on the tube before the tube is inserted into the chamber of the discharge device. For this purpose, for example, snap-in arms, with which the puncturing element is fastened movably to the tube, can be provided on the puncturing element.

The opening device preferably comprises a guide means for guiding the puncturing element from the first position into the second position. The guide means here may be provided directly on the tube. However, it is also possible to provide the guide means on a guide element which can be placed onto the tube at the end with the covering, in which case the puncturing element can then be arranged on the guide element. The guide element can be screwed, for example, onto a thread which is provided around the dispensing opening on the rigid region of the tube. However, it is also possible to provide a different connection, for example a snap-in connection or a bayonet connection, between the guide element and the tube.

The guide means can be designed, for example, as a cylindrical guide element which has a first positioning means and a second positioning means distributed along the cylinder axis, said positioning means serving to position the puncturing element on the tube. The positioning means can be provided, for example, as channels, grooves, edges or projections on the outer circumference of the guide element. In this case, the first positioning means is provided further away from the covering of the tube opening than the second positioning means. The distance between the first and the second positioning means is coordinated with the displacement distance required so that the puncturing element can pierce the covering of the tube opening.

The puncturing element, with the snap-in arms in the first position, can engage, for example, in a first channel and can be released from said engagement position by the advancing of the tube and displaced until the snap-in arms engage in a second channel. The interaction of the channels and the snap-in arms can also act as a stop for the advancing of the tube in the chamber such that said tube is prevented from being advanced further.

The puncturing element may have, for example, a disk-shaped base with a central passage, said base serving as a holder for the cannula or the spike and the fastening means, such as the snap-in arms, for fastening to the tube. The cannula or the spike can be arranged centrally on the base, and the snap-in arms can be provided, for example, along the circumference of the base such that they can engage around the guide element or the tube in the region of the opening. The snap-in arms can have inwardly protruding projections and are pre-stressed elastically in such a manner that they snap into the positioning means of the guide means when the puncturing element is pushed onto the guide means or the tube. In the process, the projections of the snap-in arms can engage in the channels of the positioning means. In order to facilitate detachment from the snapped-in position, oblique surfaces which run obliquely with respect to the longitudinal axis can be provided on the inwardly protruding projections of the snap-in arms, along which oblique surface the snap-in arms are guided as soon as an advancing force moves them in the direction of the tube. In the process, the snap-in arms are expanded and displaced along the outer circumference of the guide element or the tube until they engage in the second channel of the positioning means of the guide means.

According to a preferred embodiment of the present invention, the discharge device is provided in the form of a double chamber syringe. A tube which contains a first component, for example a solvent, is provided in one of the chambers, and a second component, for example a bone cement component, is accommodated in the other chamber. A double piston is provided for the double chamber syringe, each piston of which projects into one of the two chambers of the double chamber syringe and advances a stopper in the chamber, or in the tube. The double piston has two piston rods which are connected to each other at their rear end and form an actuating surface for a user's thumb. At the front end which lies opposite the end with the double piston, each chamber of the double syringe has a discharge opening. A discharge nozzle, preferably a mixing nozzle, into which the first and the second component can be discharged by advancing of the double piston, can be provided over the discharge opening. By continued advancing of the double piston, the two components are also advanced in the discharge nozzle and, in the case of a mixing nozzle, are mixed with each other, for example, to form a bone cement which is ready for use. The nozzle has an opening from which the mixture produced emerges from the discharge nozzle.

The length of the piston rods of the double piston, which piston rods project into the respective chambers, is coordinated in such a manner that, before a component is discharged from one of the chambers, the covering of the opening of the tube is pierced by means of the puncturing element and is therefore opened.

For this purpose, the guide element can first of all be placed, for example screwed, on the tube over the rigid region with the covered opening. The opening device, for example in the form of the puncturing element, is arranged on the outer circumferential surface of the guide element. The puncturing element engages by means of the snap-in arms in a first, front channel on the outer circumference of the guide element. The unit consisting of tube, guide element and puncturing element is inserted into the chamber of the double chamber syringe. The double piston is subsequently inserted into the two chambers. By advancing of the double piston, the piston acts on the stopper of the tube, as a result of which the tube is advanced relative to the chamber in the direction of the discharge opening of the chamber. The tube is advanced until the puncturing element strikes against a stop in the form of the bottom of the chamber. The double piston continues to be advanced, as a result of which the tube together with the guide element is displaced further relative to the puncturing element, since the puncturing element is retained against the stop of the chamber. The puncturing element is displaced from the first position, in which it comes to lie in front of the covering of the tube opening, into the second position, in which it pierces the covering. For this purpose, the guide element has an opening through which the puncturing element can be guided onto the covering.

In said second position, a fluid connection is produced between the interior of the tube and the discharge opening of the chamber, and therefore the component can be discharged from the tube through the tube opening and the discharge opening of the chamber into the discharge nozzle. By further advancing of the double piston, the first component is then discharged from the tube and at the same time the second component from the second chamber of the double chamber syringe is also discharged and ejected into the mixing nozzle.

In principle, instead of the double chamber syringe, a multichamber syringe having more than two chambers may also be used, the piston also being designed as a multiple piston.

According to the present invention, a system consisting of a discharge device and a tube, as described above, can be provided. In this case, the chamber of the discharge device is coordinated with the size of the tube, and therefore the content of the tube is permitted by advancing of the stopper within the tube by means of an advancing member.

BRIEF DESCRIPTION OF THE DRAWINGS

A preferred embodiment of the invention is illustrated below with reference to the drawings which serve merely for explanation and should not be interpreted as limiting. Features of the invention that become obvious from the drawings should be considered individually and in every combination as belonging to the disclosure of the invention. In the drawing.

Figure 1:
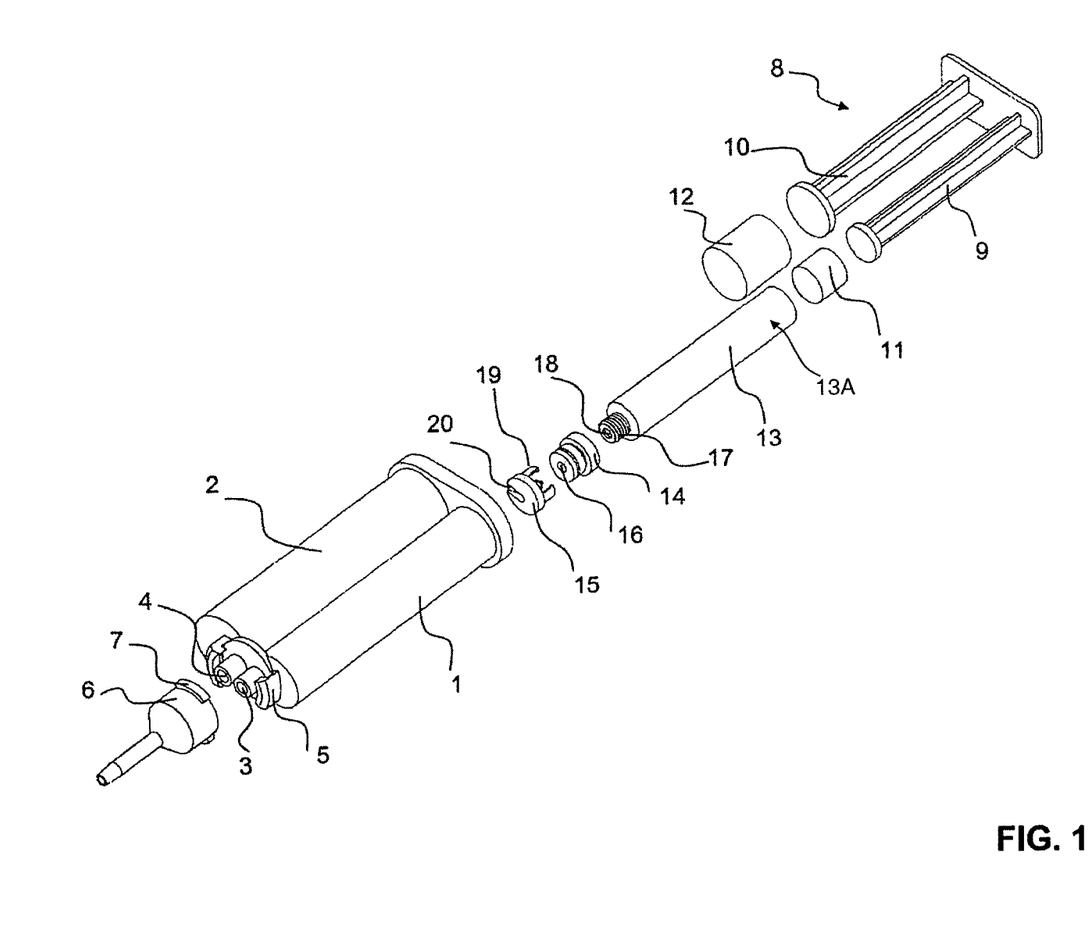
FIG. 1 shows an exploded illustration of a discharge device according to the present invention.

FIG. 1 shows an exploded illustration of a discharge device according to an embodiment of the present invention. The discharge device is in the form of a double chamber syringe which has a first chamber 1 and a second chamber 2 which are of cylindrical design and are arranged parallel next to each other. At one end, the two chambers each have a discharge opening 3 and 4, which produce a fluid connection into the interior of the chambers 1 and 2. The discharge openings 3 and 4 are arranged in parallel next to each other as cylindrical extensions. A fastening means 5 which serves to fasten a discharge nozzle 6 is provided next to the discharge openings. The fastening means 5 can be formed, for example, by retaining grooves in which retaining strips 7 attached to the discharge nozzle 6 can engage. The fastening means is preferably of detachable design such that the discharge nozzle 6 can be interchanged via the discharge openings 3 and 4. The fastening means can be provided, for example, as a bayonet connection. An advancing member in the form of a double piston 8 with a first piston rod 9 and a second piston rod 10 is provided at that end of the first and second chambers 1 and 2 which lies opposite the discharge openings 3 and 4.

A tube 13 which has a front rigid region with a closed opening 18, which region is of cylindrical design and on the outer circumference of which an external thread 17 is provided, is accommodated in the first chamber 1. The rigid region is adjoined by a cylindrical region having a deformable wall 13A. A first stopper 11 is provided for the tube 13 and a second stopper 12 is provided for the second chamber 2. The piston rods 9 and 10 of the double piston 8 respectively act on the stoppers 11 and 12. The double piston therefore serves to advance the stoppers.

A guide element 14 and an opening device in the form of a puncturing element 15 are provided on the tube 13. The guide element 14 is designed in the manner of a cylinder and has an inner passage 16 with an internal thread. The guide element 14 can be screwed by the internal thread onto the external thread 17 of the tube 13. The passage 16 therefore adjoins the opening 18 of the tube 13. The puncturing element 15 has three snap-in arms 19 which extend in the longitudinal direction of the tube 13 toward the guide element 14. The puncturing element 15 is described in more detail in FIGS. 3 to 6.

Figure 2:
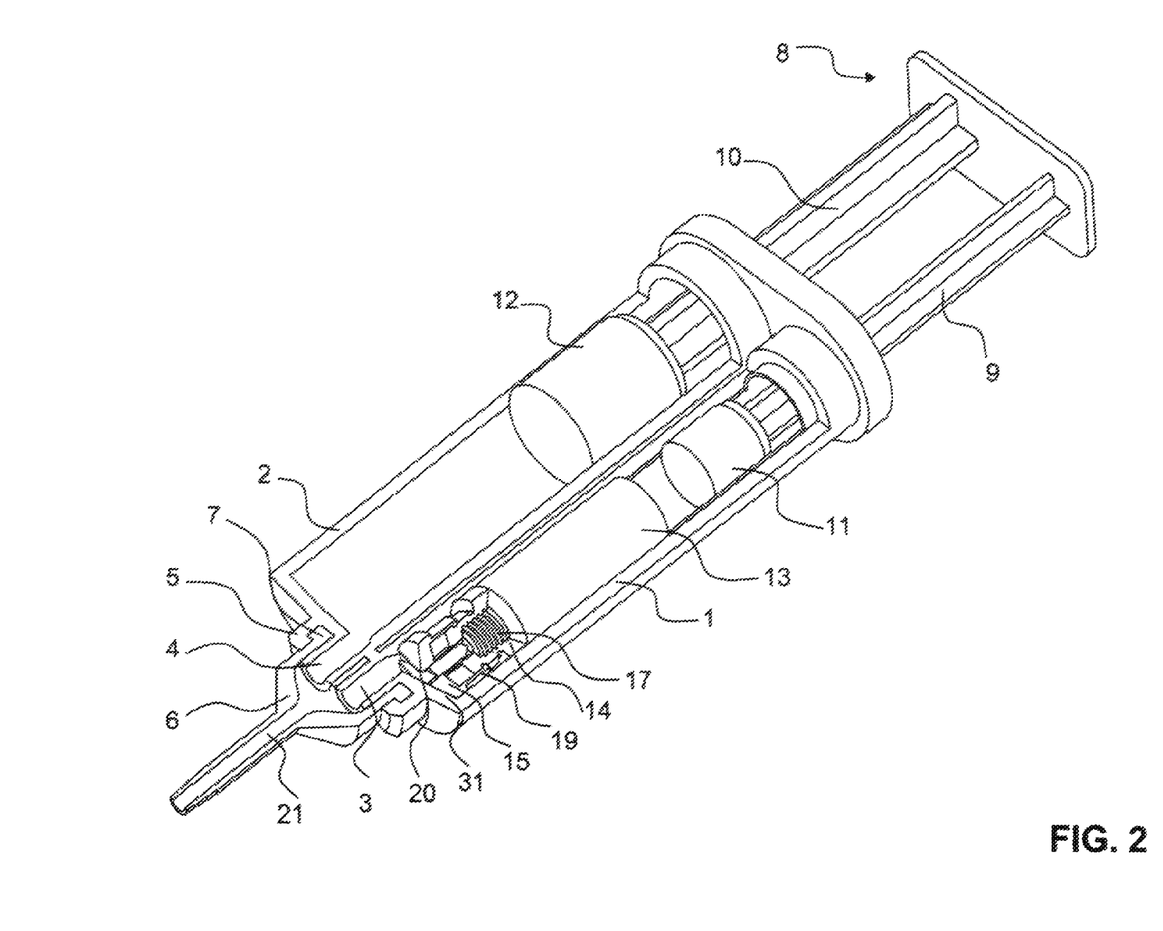
FIG. 2 shows a partial longitudinal section through an assembled discharge device according to FIG. 1.

FIG. 2 shows the discharge device according to FIG. 1 in the assembled state. In this case, the guide element 14 is screwed onto the thread 17 of the tube 13 and the puncturing element 15 is snapped onto the guide element 14 by means of the snap-in arms 19. The unit consisting of the tube 13, guide element 14 and puncturing element 15 is inserted into the first chamber 1 of the double chamber syringe. The first stopper 11 closes that end of the tube 13 which lies opposite the opening 18. The first stopper 11 is mounted displaceably in the tube 13 and closes off the tube 13 in a liquidtight manner. The second stopper 12 is mounted displaceably in the second chamber 2 and closes off the second chamber 2 in a liquidtight manner. A first component of a mixing substance is stored between the opening 18 of the tube 13 and the stopper 11, and a second component of the mixing substance is stored in the second chamber 2 between the outlet opening 4 and the second piston 12. The stoppers 11 and 12 are adjoined by the first piston rod 9 and the second piston rod 10 of the double piston 8 in such a manner that said stoppers project at one end into the first chamber 1 and the second chamber 2 and protrude from the chambers at the opposite end. By actuation, or advancing, of the double piston 8 into the chambers 1 and 2, the stoppers 11 and 12 can be moved toward the discharge openings 3 and 4 in the longitudinal direction of the chambers. Furthermore, the tube 13 can be displaced axially within the first chamber by the piston rod 9, and therefore the piston rod 9 also serves as an actuating element for advancing the tube within the chamber.

As is apparent in FIGS. 1 and 2, the puncturing element 15 has a base disk, wherein the snap-in arms 19 protrude substantially perpendicularly from said base disk. Three snap-in arms 19, which are distributed uniformly at the edge of the base disk around the circumference of the base disk, are provided. If the puncturing element 15 is placed onto the guide element 14, the snap-in arms 19 come to lie on the outer circumference of the guide element 14 and, in the process, are expanded radially elastically. The puncturing element 15 is retained on the guide element 14 by the elastic prestressing of the snap-in arms 19. The center of the base disk of the puncturing element 15 has a passage which opens out into a duct 20 which is designed as a recessed channel and runs radially from the center to the outer edge of the disk. As is apparent in FIG. 2, the puncturing element 15 is arranged on the tube 13 in such a manner that the duct 20 opens out into the discharge opening 3 when the tube 13 is inserted into the first chamber 1. This results in a fluid connection from the passage 16 of the guide element 16 to the duct 20 of the puncturing element 15 and as far as the discharge opening 3 of the chamber 1. The discharge nozzle 6 is fastened by the retaining strip 7 thereof in the fastening means 5. The two discharge openings 3 and 4 therefore open out into a discharge duct 21 of the discharge nozzle 6.

Figure 3:
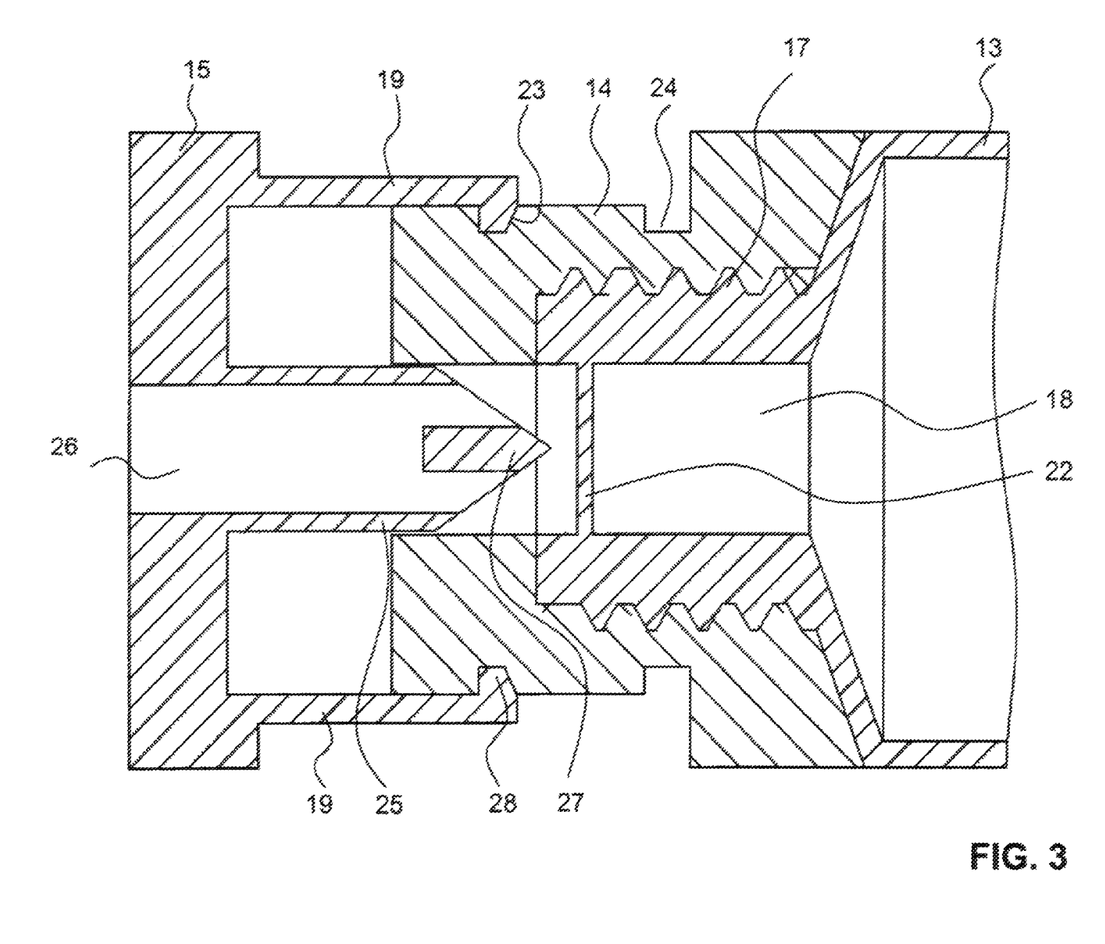
FIG. 3 shows a longitudinal section through a detailed view of the discharge device in a first position.

FIG. 3 shows a detailed longitudinal section through the puncturing element 15, the guide element 14 and the end of the tube 13 with the opening 18. The opening 18 of the tube 13 is closed by a covering 22 which can be severed or pierced. The guide element 14 is screwed onto the external thread 17 of the tube. The guide element 14 has positioning means on the outer circumference thereof, a first guide channel 23 and, offset in the longitudinal direction with respect thereto, a second guide channel 24, said guide channels extending around the circumference of the guide element. In the exemplary embodiment shown, the first guide channel 23 of the guide element 14 comes, in the longitudinal direction of the tube 13, to lie in front of the covering 22 and the second guide channel 24 comes to lie behind the covering 22.

The puncturing element 15 has the snap-in arms 19 on its outer edge. An elongate spike 25, which protrudes substantially perpendicularly from the base disk of the puncturing element 15 in the direction of the tube 13, is provided in the center of the puncturing element 15. The spike 25 has a passage line 26. At a spike end oriented in the direction of the tube 13, the center of the spike has a puncturing point 27 which serves to pierce or sever the covering 22 of the tube opening 18. The design of the puncturing point is explained more precisely in FIG. 6.

FIG. 3 shows the unit consisting of the tube 13, guide element 14 and puncturing element 15 in a first position which corresponds to a starting position. In the starting position, the point 27 of the spike 25 comes to lie just in front of the covering 22. The tube can be stored in this position for a prolonged period of time. The snap-in arms 19 of the puncturing element are pushed in the longitudinal direction over the guide element 14 and snap by means of inwardly directed projections 28 into the first guide channel 23 of the guide element 14. The puncturing element 15 is securely retained on the guide element 14 in said snapped-in position and cannot be moved in the direction of the covering 22 without further application of force.

Figure 4:
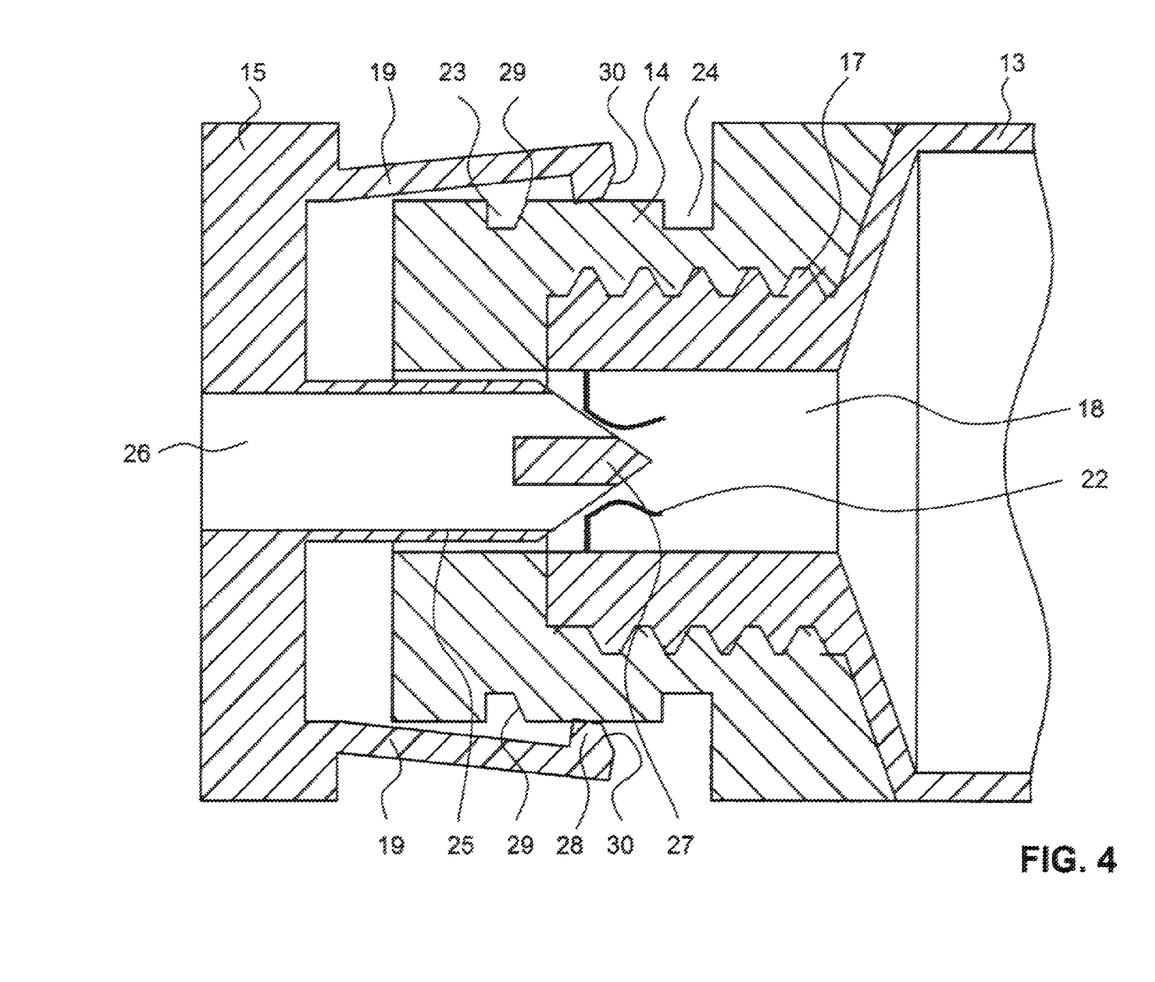
FIG. 4 shows a longitudinal section through the detailed view from FIG. 3 in a partially advanced position.

FIG. 4 shows the unit consisting of the tube 13, guide element 14 and puncturing element 15 in a transition position. In the transition position, the tube 13 with the guide element 14 fixedly attached thereto is being displaced in the longitudinal direction relative to the puncturing element 15 onto the puncturing element. In the process, the snap-in arms 19 have been expanded radially outward and moved out of the first guide channel 23 such that they come to lie on the outer circumference of the guide element 14. The first guide channel 23 has an oblique surface for this purpose. The first guide channel 23 therefore widens outward towards the circumference of the guide element 14. The projections 28 of the snap-in arms 19 have an oblique surface 30 corresponding to the oblique surface 29. The projection 28 therefore converges inward in a manner tapering in the direction of the guide element 14. In FIG. 3, the oblique surfaces 29 of the first guide channel 23 and the oblique surfaces 30 of the projections 28 of the snap-in arms 19 come to lie on one another. If a force is exerted on the tube 13 with the guide element 14 in the direction of the puncturing element 15, the oblique surfaces slide off from one another and, in the process, expand the snap-in arms 19, as is apparent in FIG. 4. By means of the relative movement between the tube 13 and the puncturing element 15, the spike 25 of the puncturing element 15 has moved in the direction of the covering 22 and has severed the latter. In the process, the spike 25 has been introduced into the opening 18 of the tube 13 to an extent such that the puncturing point 27 has pierced the covering 22.

Figure 5:
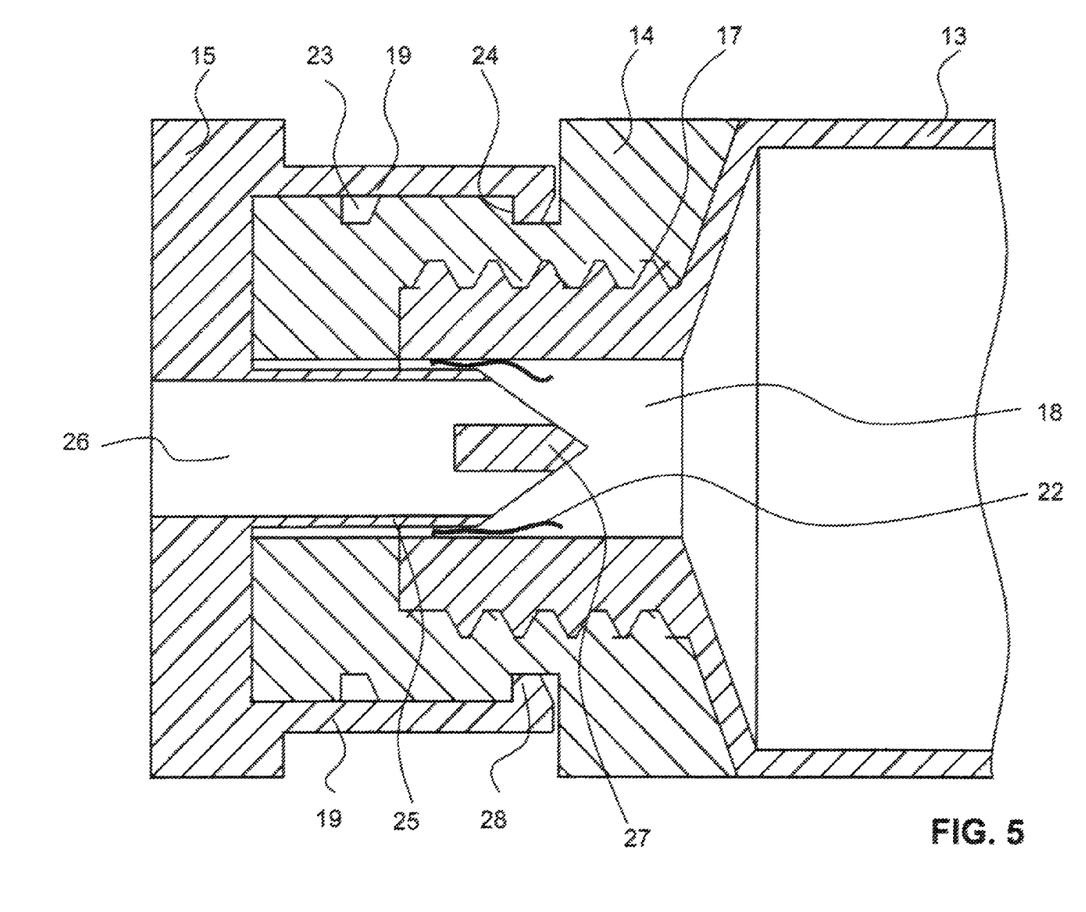
FIG. 5 shows a longitudinal section through a detailed view of the discharge device in a second position.

FIG. 5 shows the unit consisting of the tube 13, guide element 14 and puncturing element 15 in a second position in which the puncturing element 15 has been displaced longitudinally relative to the tube 13 and the covering 22 has been pierced. The second position corresponds to a piercing position. In comparison to the position according to FIG. 4, the tube 13 with the guide element 14 has been displaced further in the direction of the puncturing element 15. In the process, the projections 28 of the snap-in arms 19 of the puncturing element 15 slide on the outer circumference of the guide element 14 in the direction of the tube 13 until they snap into the second guide channel 24. In this position, the puncturing element 15 is attached fixedly to the guide element 14. The surfaces of the projections 28 and of the second guide channel 24, which surfaces come to lie on each other in the longitudinal direction, run substantially perpendicularly to the longitudinal direction of the guide element. If it is attempted to pull the puncturing element 15 off the guide element 14, said surfaces are pressed against each other but the snap-in arms 19 are not expanded radially outward. In this position, the puncturing element 15 comes to lie on the guide element 14 in such a manner that the fluid connection between the opening 18 of the tube 13 and the passage line 26 of the puncturing element 15 is liquidtight. The front side of the guide element 14 comes here to lie on the base disk of the puncturing element 15 and the inner circumference of the passage 16 of the guide element 14 comes to lie on the outer circumference of the spike 25. It is possible for, for example, sealing means, for example a rubber coating or a rubber ring, to be provided between the surfaces which come to lie on each other.

In FIG. 5, a fluid connection is produced between the interior of the tube 13 along the opening 18 to the passage line 26 and to the duct 20 (not shown in FIG. 5) and therefore forms a connecting device between the chamber opening 3 and the dispensing opening 18 of the tube 13. The first component of the mixing substance can therefore be discharged from the tube 13.

Figure 6:
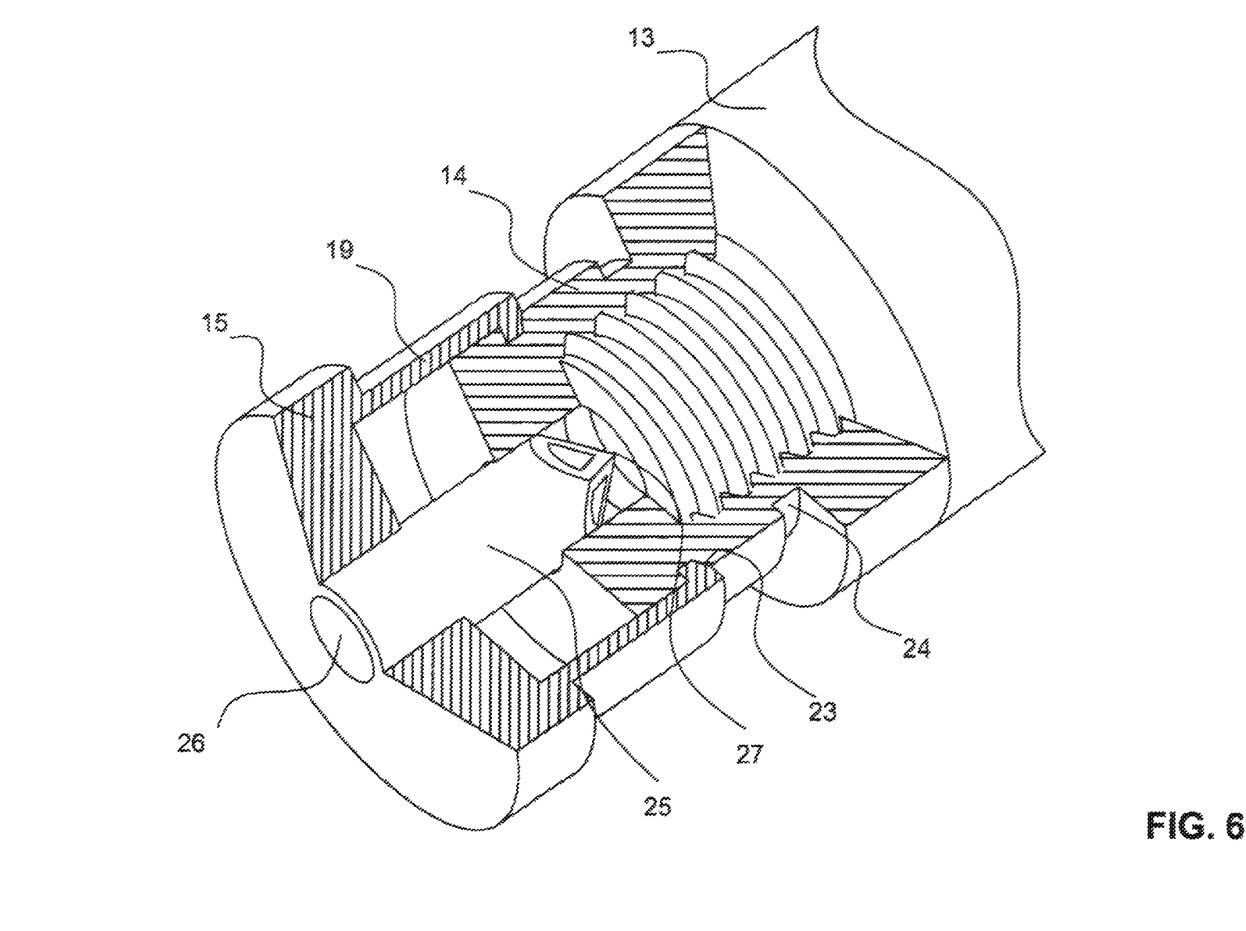
FIG. 6 shows a three-dimensional illustration of the detailed view according to FIG. 3.

FIG. 6 shows a three-dimensional view with a partial section through the unit consisting of the tube 13, guide element 14 and puncturing element 15. This view shows the unit in the first position, in which the snap-in arms 19 of the puncturing element 15 are snapped into the first guide channel 23 of the guide element 14. The spike 25 of the puncturing element 15 projects centrally in the direction of the tube 13. The puncturing point 27 is formed by webs which converge inward in a pointed manner and protrude from the outer circumference of the spike 25 as far as the center point of the passage line 26. Passages into the interior of the passage line 26 remain between the individual webs and the circumferential wall. The webs are of angular design on the outside thereof such that they form the puncturing point 27 in the center point of the spike.

The sequence of use of a discharge device according to the present invention can be explained with reference to FIG. 2. In FIG. 2, the discharge device in the form of the double chamber syringe is in the first position, the starting position. The first piston rod 9 adjoins the first stopper 11 in the tube 13. The first component of the mixing substance is located in the tube 13 between the opening 18, which is closed by the covering 22, and the first stopper 11. In order to produce the mixture using the double chamber syringe, the syringe body containing the first chamber 1 and the second chamber 2 can be grasped, for example, with the fingers while the thumb comes to lie on the double piston 8. The double piston 8 can therefore be displaced relative to the chambers of the double chamber syringe and into said chambers. In this case, an advancing force is exerted on the first stopper 11, said advancing force being transmitted via the first component of the mixing substance to the tube 13 such that the tube 13 is displaced relative to the first chamber 1 in the direction of the discharge opening 2. In FIG. 2, the tube 13 has already been advanced to an extent such that the puncturing element 15 strikes against a bottom wall 31 of the first chamber 1. The bottom wall 31 forms a stop for the advancing of the unit consisting of the tube 13, guide element 14 and puncturing element 15. Upon further advancing of the double piston 8, the advancing force therefore acts on the snap-in arms 19 of the puncturing element 15, which snap-in arms retain the puncturing element 15 on the guide element 14. As described in FIGS. 4 and 5, the snap-in arms 19 are expanded radially outward along the oblique surfaces 29 and 30 by the advancing force such that the tube 13 and the guide element 14 can be displaced relative to the puncturing element in the direction of the bottom wall 31, or the discharge opening 3. The tube 13 is displaced relative to the puncturing element 15 until the snap-in arms 19 snap into the second guide channel 24 of the guide element 14. At the same time, the front side of the guide element 14 strikes against the disk-shaped region of the puncturing element 15. During said advancing movement, the covering 22 of the opening 18 of the tube 13 is severed by the puncturing point 27 of the spike 25 of the puncturing element 15.

The discharge device is now in the second position, in which a fluid connection is formed between the interior of the first chamber 1 and the discharge opening 3, and the discharge duct 21, of the discharge nozzle 6. By further advancing of the double piston 8, the first stopper 11 is advanced in the tube 13 and the second stopper 10 is advanced into the second chamber 2 such that the first and second components of the mixing substance are emptied at the same time from the first and second chambers through the discharge openings 3 and 4 into the discharge nozzle 6. The components are mixed with each other in the discharge nozzle 6. For this purpose, it is possible to provide additional mixing means in the discharge nozzle 6. By continued advancing of the double piston 8, the mixture is discharged from the discharge device through the discharge duct 21 from the discharge nozzle 6.

During the advancing of the stopper 11 in the tube 13, the stopper is displaced relative to the deformable wall of the tube, wherein the inner circumference of the chamber 1 comes to lie on the outer circumference of the tube 13 and supports the tube 13 against deformation or collapsing.

In an alternative embodiment, the opening mechanism can also be realized by a cannula or the like fastened in the chamber. According to the invention, the tube can also be opened prior to insertion into the chamber 1 of the discharge device such that, by advancing of the advancing member in the form of the double piston 8, the content of the tube can be immediately discharged. In this case, a fluid connection is produced, for example, by the tube pressing against the chamber bottom, in which case the dispensing opening of the tube and the discharge opening of the chamber adjoin each other. The opening mechanism, as has been described above, can advantageously be used not only in tubes but also in other containers which have a closed or covered opening. For example, cartridges or the like can also be opened with an opening mechanism of this type. Provision is therefore made for a patent claim directed to the feature of the opening device independently of the use in tubes.

LIST OF REFERENCE NUMBERS

1 First chamber
2 Second chamber
3 Discharge opening, first chamber
4 Discharge opening, second chamber
5 Fastening means
6 Discharge nozzle
7 Retaining strips
8 Double piston
9 First piston rod
10 Second piston rod
11 First stopper
12 Second stopper
13 Tube
14 Guide element
15 Puncturing element
16 Passage, guide element
17 External thread
18 Opening, container
19 Snap-in arms
20 Duct
21 Discharge duct
22 Covering
23 First guide channel
24 Second guide channel
25 Spike
26 Passage line
27 Puncturing point
28 Projection
29 Oblique surface, guide channel
30 Oblique surface, projection
31 Bottom wall

The invention claimed is:

1. A discharge device being designed as a multiple syringe for discharging a fluid, first product from at least one first container, comprising:
 a first container in the form of a tube with a dispensing opening and a cylindrical region having a deformable wall;
 a movable stopper arranged in the tube, said stopper being arranged at the end opposite the dispensing opening and closing said end of the tube;

a housing having at least one first chamber which has a first chamber opening and in which the first container is accommodated and at least one second chamber which has a second chamber opening and in which a second product is accommodated;

a movable first advancing member for discharging the first product; and a second advancing member which is arranged movably in the second chamber;

the first and the second advancing members being connected to each other at a rear end facing away from the first and second chamber opening, in order to prevent a relative motion between the first and the second advancing members, the first advancing member being adapted to be joined to the stopper and being movable within the tube in the direction of the dispensing opening in order to discharge the fluid, first product from the tube, wherein the dispensing opening of the tube is closed by a pierceable covering, wherein, in the discharge device, an opening device which is displaceable relative to the tube is provided, with a puncturing element for piercing the covering, wherein the tube is arranged movably in the first chamber of the discharge device in such a manner that the puncturing element pierces the covering upon movement of the tube in the direction of the first dispensing opening, and wherein the first and the second advancing member are dimensioned in such a manner that, upon joint advancing of the advancing members, the first advancing member moves the tube in the direction of the first dispensing opening, and as a result, the puncturing element pierces the covering of the tube before the second advancing member ejects the second product from the second chamber.

2. The discharge device as claimed in claim 1, wherein the housing is designed to be grasped between the fingers of a hand of a user, and wherein the first advancing member is arranged in such a manner that it can be actuated with the thumb of the same hand with which the housing is grasped, in order to manually advance the first advancing member to discharge the first product.

3. The discharge device as claimed in claim 1, wherein an external thread which surrounds the dispensing opening is formed on the tube.

4. The discharge device as claimed in claim 1, wherein a connecting device is provided, the connecting device connecting the first chamber opening to the dispensing opening of the tube.

5. The discharge device as claimed in claim 1, wherein an actuating element is provided for effecting joint advancing of the first and second advancing members.

6. The discharge device as claimed in claim 5, wherein the actuating element is operative with the first advancing member for advancing the stopper in the tube.

7. The discharge device as claimed in claim 1, wherein the opening device, in a first position, is adapted to be advanced together with the tube relative to the first chamber and, in a second position, abuts in the advancing direction against a stop of the first chamber, in which case said opening device is stationary relative to the first chamber and displaceable relative to the tube.

8. The discharge device as claimed in claim 1, wherein the opening device has an inner passage line which serves as a connecting device.

9. The discharge device as claimed in claim 1, wherein a guide element is provided for guiding the opening device from a first position into a second position relative to the tube and is adapted to be screwed onto the tube at the end with the covering, and the opening device being arranged on the guide element.

* * * * *